(12) United States Patent
Dudhara et al.

(10) Patent No.: US 8,012,496 B2
(45) Date of Patent: *Sep. 6, 2011

(54) GASTRIC RETENTION CONTROLLED DRUG DELIVERY SYSTEM

(75) Inventors: Kamlesh Mohanlal Dudhara, Baroda (IN); Nitin Bhalachandra Dharmadhikari, Mumbai (IN); Vaishali Vijay Dhavse, Mumbai (IN)

(73) Assignee: Sun Pharma Advanced Research Company Ltd., Andheri (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/856,097

(22) Filed: Aug. 13, 2010

(65) Prior Publication Data

US 2010/0305208 A1 Dec. 2, 2010

Related U.S. Application Data

(63) Continuation of application No. 10/482,770, filed as application No. PCT/IN02/00144 on Jul. 4, 2002, now Pat. No. 7,776,345.

(30) Foreign Application Priority Data

Jul. 4, 2001 (IN) ............................ 612/MUM/2001

(51) Int. Cl.
*A61K 9/00* (2006.01)
*A61K 9/24* (2006.01)
*A61K 31/195* (2006.01)
*A61P 7/00* (2006.01)

(52) U.S. Cl. ...................... 424/400; 424/471; 514/567

(58) Field of Classification Search ................. 424/400, 424/471; 514/467
See application file for complete search history.

(56) References Cited

U.S. PATENT DOCUMENTS

| | | |
|---|---|---|
| 4,101,650 A | 7/1978 | Umezawa |
| 4,772,473 A | 9/1988 | Patel et al. |
| 4,777,033 A | 10/1988 | Ikura et al. |
| 4,824,678 A | 4/1989 | Lindahl et al. |
| 4,844,905 A | 7/1989 | Ichikawa et al. |
| 4,892,739 A | 1/1990 | Shah et al. |
| 4,996,058 A | 2/1991 | Sinnreich |
| 5,091,184 A | 2/1992 | Khanna |
| 5,096,714 A | 3/1992 | Kuhrts |
| 5,651,985 A | 7/1997 | Penners et al. |
| 5,654,005 A | 8/1997 | Chen et al. |
| 6,261,601 B1 | 7/2001 | Talwar et al. |
| 6,340,475 B2 | 1/2002 | Shell et al. |
| 6,960,356 B1 | 11/2005 | Talwar et al. |
| 7,109,239 B2 | 9/2006 | Gallop et al. |
| 7,776,345 B2 * | 8/2010 | Dudhara et al. ............... 424/400 |
| 2007/0265343 A1 | 11/2007 | Dharmadhikari et al. |

FOREIGN PATENT DOCUMENTS

| | | |
|---|---|---|
| EP | 1095650 | 5/2001 |
| JP | 63014715 A | 1/1988 |
| WO | 98/51408 | 11/1998 |
| WO | 99/47128 A1 | 9/1999 |
| WO | 00/15198 | 3/2000 |
| WO | 00/15198 A1 | 3/2000 |
| WO | 00/23045 | 4/2000 |
| WO | 00-38650 | 7/2000 |
| WO | 00/38650 | 7/2000 |
| WO | 01/08670 A2 | 2/2001 |
| WO | 01/10417 A1 | 2/2001 |
| WO | 01/10419 A1 | 2/2001 |

OTHER PUBLICATIONS

M. Merino et al.; "Evidence of a Specialized Transport Mechanism for the Intestinal Absorption of Baclofen"; Biopharmaceutics & Drug Disposition; Apr. 26, 1988; vol. 10; pp. 279-297; John Wiley & Sons, Ltd.; c. 1989.

M. Merino et al.; "Evidence of Specialized Absorption Mechanism for Baclofen"; Department of Pharmacology and Pharmaceutics, University of Valencia, Valencia, Spain; pp, 564-573, 1987.

* cited by examiner

*Primary Examiner* — Robert A Wax
*Assistant Examiner* — Aradhana Sasan
(74) *Attorney, Agent, or Firm* — Sughrue Mion, PLLC

(57) ABSTRACT

The present invention provides a gastric retention controlled drug delivery system comprising:
(a) a controlled release core comprising a drug, a highly swellable polymer and a gas generating agent, said core being capable of swelling and achieving floatation rapidly while maintaining its physical integrity in gastrointestinal fluids for prolonged periods, and
(b) a rapidly releasing coat composition comprising the same drug as in the core and pharmaceutically acceptable excipients, wherein the coating composition surrounds the core such that the system provides a biphasic release of the drug in gastrointestinal fluids.

1 Claim, 1 Drawing Sheet

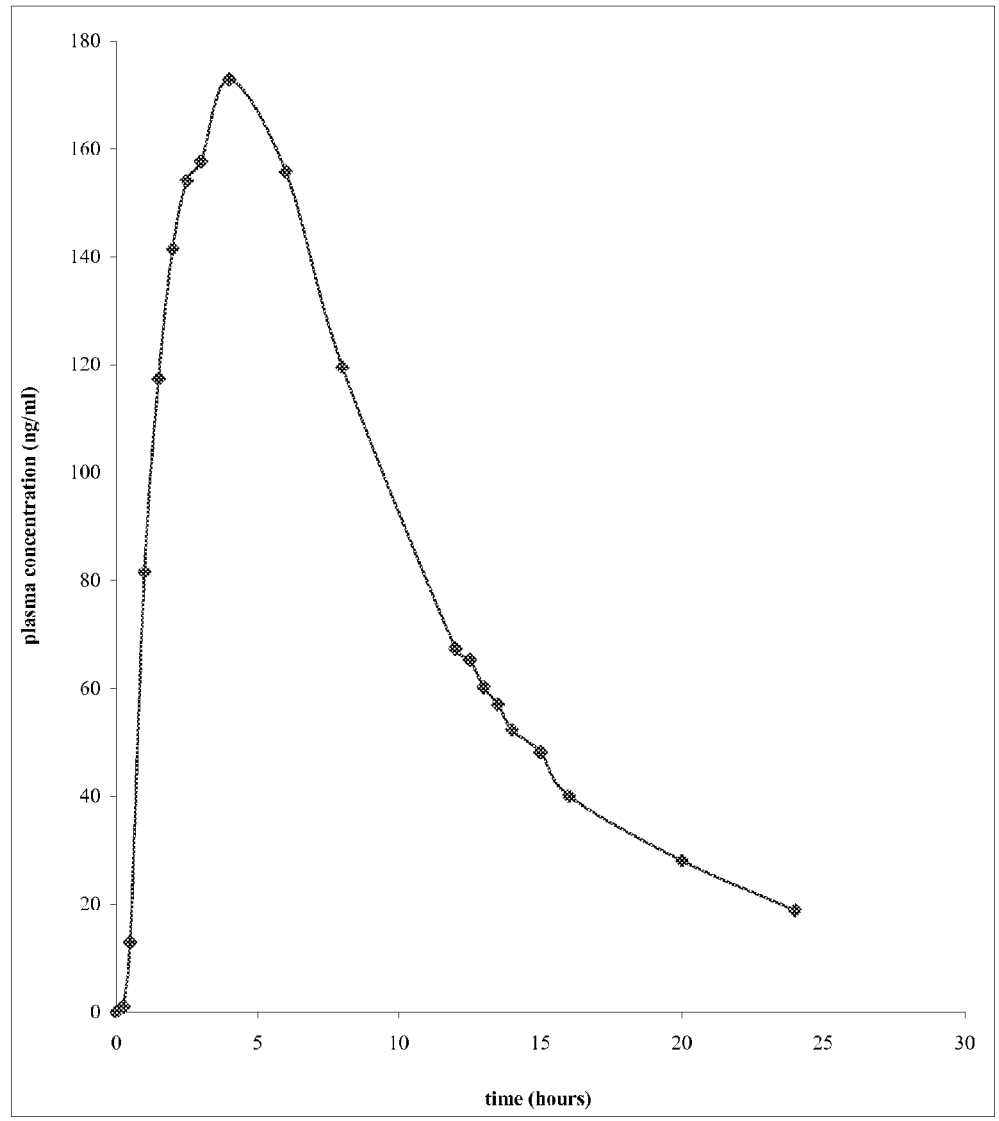

GASTRIC RETENTION CONTROLLED DRUG DELIVERY SYSTEM

CROSS REFERENCE

This is a Continuation of U.S. patent application Ser. No. 10/482,770, filed on Dec. 31, 2003, which is a 371 of PCT Application No. PCT/IN02/00144 filed Jul. 4, 2002, which claims priority from Indian Patent Application No. 612/MUM/2001 filed Jul. 4, 2001, all of which applications are incorporated herein by references.

FIELD OF THE INVENTION

The present invention relates to a gastric retention controlled drug delivery system having a biphasic release pattern.

BACKGROUND OF THE INVENTION

Controlled drug delivery systems deliver drug to the body so as to establish therapeutically effective blood levels of the active ingredient and once these blood levels are achieved they continue to maintain constant blood levels for long durations by delivering the drug to the body at the same rate as the body eliminates the drug. By avoiding peaks and troughs in blood levels associated with conventional dosage forms, controlled drug delivery systems lower the incidence of adverse effects or side effects. Very importantly controlled drug delivery systems reduce the frequency of dosing leading to convenience to the patient in terms of dosing and compliance to the specified dosage regimens.

It is generally known that the rate at which an oral controlled drug delivery system delivers the drug into the blood is not the same as the rate at which it releases the drug into a test aqueous fluid because the gastrointestinal fluid's pH, composition and agitation intensity change with the specific location of the drug delivery system in the gastrointestinal tract i.e. from the stomach to the colon, fasted versus fed state, type and amount of food ingested, and also vary from individual to individual. In addition, the drug may not be absorbed in the same manner and propensity we move from the stomach to the colon. Some drugs have an "absorption window" i.e. they are absorbed only from the upper parts of the gastrointestinal tract, whereas there are others whose absorption from the colon is not uniform or complete. Thus, the location of the controlled drug delivery system in the gastrointestinal tract as well as the rate at which the controlled drug delivery system moves from the stomach to the colon represent important factors that need to be considered in the design of an oral controlled drug delivery system. It is thus known to those skilled in the art that an oral controlled delivery should be designed not only with a control on the rate at which it releases the drug over the drug delivery time period (temporal control) but also a control on the location from which it is delivered (spatial control). The spatial control can be achieved by prolonging the period of retention of the system in the stomach. Gastric retention systems are also beneficial when the drug is effective locally in the stomach. Drugs absorbed in the upper part of the gastrointestinal tract may exhibit variability in absorption due to inter and intra-individual variability in gastric emptying and gastrointestinal motility. This variation in absorption may be addressed by administering a dosage form comprising the drug such that a small part of the drug is available as immediate release, and a large part is available as sustained or controlled release.

One of the approaches that has been used for achieving spatial control involves increasing the gastric retention of sustained or controlled drug delivery systems by using a composition containing highly swellable polymers in admixture with a gas-generating agent to form systems that are large in size as well as capable of floating on gastric fluids. It has now become well recognized by those particularly skilled in the art that systems containing swellable polymers will instantly float on gastric fluids because the gas generated and entrapped within the system decreases the density. Swelling to a large size is an important factor in gastric retention of the system. Solids having a size less than 5 to 7 mm show delayed gastric emptying in fed conditions but they can still be emptied from the stomach because their size is smaller than the pyloric sphincter. Even floating systems of size less than 5 to 7 mm can be emptied if the patient is in supine position. The mean resting pyloric diameter is approx. 13+7 mm and it has been reported that dosage forms with a size of approx. 12-18 mm diameter in their expanded state would generally be excluded from the passage of the pyloric sphincter. The system should also be capable of retaining this size in the gastric fluids for long periods under agitational conditions created by gastric motility. Such large intact systems cannot be emptied until the arrival of the interdigestive migrating motor complex at the beginning of the interdigestive phase. The combination of increase in size and floatation results in increased gastric retention of the system. The prior art resulting in this current state of the art is described below.

U.S. Pat. No. 4,101,650 ('650) assigned to Zaidan Hojin Biseibutsu Kagaku Kenkyu Kai discloses a formulation in which granules containing sodium bicarbonate, lactose and polyvinylpyrrolidone are coated with a layer of hydroxypropyl methylcellulose. These are then further coated with a suspension containing the active ingredient pepstatin and hydroxypropyl methylcellulose to form floating minicapsules of a diameter in the range of 0.1 to 2 mm. The drawback of this system is that the minicapsules are much smaller in size than required for long durations of retention in the stomach.

U.S. Pat. No. 4,777,033 ('033) assigned to Teijin Limited, discloses an oral sustained release pharmaceutical preparation comprising a lower alkyl ether of cellulose, polyacrylic acid or its pharmaceutically acceptable salt, a drug, and an effective amount of effervescent foaming agent. Tablets made from the composition however still retained the above-cited major disadvantages associated with the '650 prior art in that the tablets of the '033 system did not remain intact when subjected to dissolution testing.

U.S. Pat. No. 4,844,905 assigned to Eisai Co. discloses granules comprising a drug containing core; a middle gas-generating layer comprising sodium carbonate and organic acid; and an outer coat of an expandable polymer film. Although intended for remaining in the stomach, the granules have the disadvantage of small size.

Japanese Patent No. 63014715 assigned to Zeria Shinyaku Kogyo KK discloses a slow releasing composition comprising (A) a high-viscosity water-soluble polymer, preferably cellulose ether or polyvinyl alcohol, (B) crosslinked insoluble polyvinyl pyrrolidone, and (C) a component to foam in contact with gastric juice, preferably carbonate, especially calcium carbonate or precipitated calcium carbonate. The system does not however contain a part of the drug in immediate release form and a part in controlled release form and does not provide a biphasic release pattern. Thus, even at the start of the dosage regimen when there is no drug available in the body, the system may begin with a relatively slow rate of release as compared to that from an immediate release composition. Another disadvantage is that whereas polymers that are highly swellable as well as rapidly swellable may be desirable for achieving gastric retention, we have found that several cellulose ethers do not conform to these requirements.

U.S. Pat. No. 5,651,985 assigned to Bayer AG, claims a pharmacologically active composition comprising a pharmacologically active compound dispersed in a homogenous mixture on the molecular level of polyvinylpyrrolidone and a methacrylic acid polymer having an acidic number between 100 and 1,200 mg of KOH/g of polymer solid substance, and optionally a gas-forming additive. The system does not however contain a part of the drug in immediate release form and a part in controlled release form and does not provide a biphasic release pattern. The rate of swelling of these systems is also slow so that they do not achieve the desired large size in a short period of 15 to 30 minutes. Moreover in order to achieve homogeneity of the two polymers on the molecular level a cumbersome and expensive process such as freeze-drying is required.

PCT publication No. WO 00/15198 assigned to Ranbaxy Laboratories relates to a pharmaceutical composition comprising a drug, a gas-generating component, a swelling agent, a viscolyzing agent, and optionally a gel-forming polymer. The gas generating agents used are carbonates or bicarbonates. The swelling agent is a superdisintegrant such as cross-linked polyvinylpyrrolidone, cross-linked carboxymethylcellulose and sodium starch glycolate. The viscolyzing agent is a carbohydrate gum that viscolyzes instantly. The system does not however contain a part of the drug in immediate release form and a part in controlled release form and does not provide a biphasic release pattern.

PCT publication No. WO 01/10419 assigned to Ranbaxy Laboratories relates to a pharmaceutical composition comprising a drug, a sugar, a diluent and a gas generating agent, and PCT publication No. WO 01/10405 also assigned to Ranbaxy Laboratories relates to a pharmaceutical composition comprising a drug, inert oil, a sugar, a diluent and a gas-generating agent. These systems however are not capable of swelling to a desirable large size suitable for gastric retention, as they do not contain any swellable substance.

PCT publication No. WO 00/23045 assigned to Sanofi-Synthelabo discloses a pharmaceutical composition containing two or three layers and contains an active principle in association with an excipient modifying its release and a system capable of generating carbon dioxide in a swelling polymer hydrophilic matrix. Examples are provided where the active principle is in one layer containing swellable polymers as the excipient modifying its release and the second layer contains swellable polymer in association with a carbonate. The composition is in the form of bilayer or trilayer tablets. The system does not however contain a part of the drug in immediate release form and a part in controlled release form and does not provide a biphasic release pattern.

PCT publication No. WO 01/10417 assigned to Galenix Development discloses and claims a pharmaceutical composition containing at least one phase comprising an active principle in association with one or many excipients and a second phase called non-active, consisting of at least one gas-generating system and at least one hydrophilic polymer or a porous mineral compound; and wherein the active phase comprises at least 80% active principle. The limitation of using not more than 20% of a release rate controlling excipient limits the flexibility that a formulator has for obtaining the desired rate of release while providing a higher level of assurance of reproducibility of the release profile from batch-to-batch. On the other hand when rate-controlling excipients are chosen judiciously such that they provide a highly reproducible release profile even when used in small amounts they may not be rapidly and highly swellable themselves. The system of WO 01/10417 uses the non-active phase to achieve floatation, which is achieved by a low density resulting from entrapment of carbon dioxide in the non-active phase matrix.

OBJECT OF THE INVENTION

It is an object of the present invention to provide a gastric retention controlled drug delivery system comprising:
a. a controlled release core comprising a drug, a highly swellable polymer and a gas generating agent, said core being capable of swelling and achieving flotation rapidly while maintaining its physical integrity in gastrointestinal fluids for prolonged periods, and
b. a rapidly releasing coat composition comprising the same drug as in the core and pharmaceutically acceptable excipients, wherein the coating composition surrounds the core such that the system provides a biphasic release of the drug in gastrointestinal fluids.

Yet another specific object of the present invention is to provide a gastric retention controlled drug delivery system for baclofen.

SUMMARY OF THE INVENTION

The present invention provides a gastric retention controlled drug delivery system comprising:
(a) a controlled release core comprising a drug, a highly swellable polymer and a gas generating compound, said core being capable of swelling and achieving floatation rapidly while maintaining its physical integrity in gastrointestinal fluids for prolonged periods, and
(b) a rapidly releasing coat composition comprising the same drug as in the core and pharmaceutically acceptable excipients, wherein the coating composition surrounds the core such that the system provides a biphasic release of the drug in gastrointestinal fluids.

The present invention further provides a gastric retention controlled drug delivery system wherein the controlled release core is capable of swelling rapidly to at least about two times its original volume, and maintaining its physical integrity in gastrointestinal fluids for prolonged periods.

The present invention also provides a gastric retention controlled drug delivery system comprising baclofen or its pharmaceutically acceptable salt.

BRIEF DESCRIPTION OF THE DRAWING

FIG. 1 shows the plasma concentration vs time profile obtained upon administration of one embodiment of the gastric retention controlled drug delivery system of the present invention having 30 mg baclofen.

DESCRIPTION OF THE INVENTION

The present invention provides a gastric retention controlled drug delivery system comprising:
(a) a controlled release core comprising a drug, a highly swellable polymer and a gas generating compound, said core being capable of swelling and achieving floatation rapidly while maintaining its physical integrity in gastrointestinal fluids for prolonged periods, and
(b) a rapidly releasing coat composition comprising the same drug as in the core and pharmaceutically acceptable excipients, wherein the coating composition surrounds the core such that the system provides a biphasic release of the drug in gastrointestinal fluids.

The gastric retention controlled drug delivery system of the present invention is useful in providing improved drug delivery. Drugs that may be used in the gastric retention controlled drug delivery system of the present invention may be selected from the following, viz. alcohol abuse preparations, drugs used for alzheimer's disease, anaesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for skin ailments, steroids and hormones.

Examples of acromegaly agents are octreotide, laureotide and pegvisomant.

Examples of alcohol abuse preparations are chlorazepate, chlordiazepoxide, diazepam, disulfuram, hydroxyzine, naltrexone and their salts.

Examples of anaesthetics are adrenaline, bupivacaine, chloroprocaine, desflurane, etidocaine, levobupivacaine, lidocaine, midazolam, propofol, ropivacaine and their salts.

Examples of analgesics are acetaminophen, aspirin, bupivacain, buprenorphine, butorphanol, celecoxib, clofenadol, choline, clonidine, codeine, diflunisal, dihydrocodeine, dihydroergotamine, dihydromorphine, ethylmorphine, etodolac, eletriptan, eptazocine, ergotamine, fentanyl, fentoprofen, hyaluronic acid, hydrocodon, hydromorphon, hylan, ibuprofen, lindomethacin, ketorolac, ketotifen, levomethadon, levallorphan, levorphanol, lidocaine, mefenamic acid, meloxicam, meperidine, methadone, morphine, nabumetone, nalbuphin, nefopam, nalorphine, naloxone, naltrexone, naproxen, naratriptan, nefazodone, mormethadon, oxapozin, oxycodone, oxymorphon, pentazocin, pethidine, pehnpyramid, piritramid, piroxicam, propoxyphene, refecoxib, rizatriptan, salsalaketoprofen, sulindac, sumatriptan, tebacon, tilidin, tolmetin, tramadol, zolmitriptan and their salts.

Examples of antiasthmatics are ablukast, azelastine, bunaprolast, cinalukast, cromitrile, cromolyn, enofelast, isamoxole, ketotifen, levcromekalin, lodoxamide, montelukast, ontazolast, oxarbazole, oxatomide, piriprost potassium, pirolate, pobilukast edamine, quazolast, repirinast, ritolukast, sulukast, tetrazolastmeglumine, tiaramide, tibenelast, tomelukast, tranilast, verlukast, verofylline, zarirlukast.

Examples of anticancer agents are adriamycin, aldesleukin, allopurinol, altretamine, amifostine, anastrozole, asparaginase, betamethasone, bexarotene, bicalutamide, bleomycin, busulfan, capecitabine, carboplatin, carmustine, chlorambucil, cisplatin, cladribine, conjugated estrogen, cortisone, cyclophosphamide, cytarabine, dacarbazine, daunorubicin, dactinomycin, denileukin, dexamethasone, discodermolide, docetaxel, doxorubicin, eloposidem, epirubicin, epoetin, epothilones, estramustine, esterified estrogen, ethinyl estradiol, etoposide, exemestane, flavopirdol, fluconazole, fludarabine, fluorouracil, flutamide, floxuridine, gemcitabine, gemtuzumab, goserelin, hexamethylmelamine, hydrocortisone, hydroxyurea, idarubicin, ifosfamide, interferon, irinotecan, lemiposide, letrozole, leuprolide, levamisole, levothyroxine, lomustine, mechlorethamine, melphalan, mercaptopurine mechlorethamine, megesterol, methotrexate, methylprednisolone, methyltestosterone, mithramycin, mitomycin, mitotane, mitoxantrone, mitozolomide, mutamycin, nilutamide, paclitaxel, pamidronate, pegaspargase, pentostatin, plicamycin, porfimer, prednisolone, procarbazine, rituximab, sargramostim, semustine, streptozocin, tamoxifien, temozolamide, teniposide, testolactone, thioguanine, thiotepa, tomudex, topotecan, toremifene, trastumuzab, tretinoin, semustine, streptozolocin, valrubicin, verteprofin, vinblastine, vincristine, vindesine, vinorelbine and their salts.

Examples of anticoagulants and antithrombic agents are warfarin, dalteparin, heparin, tinzaparin, enoxaparin, danaparoid, abciximab, alprostadil, altiplase, anagralide, anistreplase, argatroban, ataprost, beraprost, camonagreel, cilostazol, clinprost, clopidogrel, cloricromen, dermatan, desirudin, domitroban, drotaverine, epoprostenol, eptifibatide, fradafiban, gabexate, iloprost, isbogrel, lamifiban, lamoteplase, lefradafiban, lepirudin, levosimendan, lexipafant, melagatran, nafagrel, nafamostsat, nizofenone, orbifiban, ozagrel, pamicogrel, parnaparin, quinobendan, reteplase, sarpogralate, satigrel, silteplase, simendan, ticlopidine, vapiprost, tirofiban, xemilofiban, Y20811 and their salts.

Examples of anticonvulsants are carbamazepine, clonazepam, clorazepine, diazepam, divalproex, ethosuximide, ethotion, felbamate, fosphenyloin, gabapentin, lamotrigine, levetiracetam, lorazepam, mephenyloin, mephobarbital, metharbital, methsuximide, oxcarbazepine, phenobarbital, phenyloin, primidone, tiagabine, topiramate, valproic acid, vigabatrin, zonisamide, and their salts.

Examples of antidiabetic agents are acarbose, acetohexamide, carbutamide, chlorpropamide, epalrestat, glibornuride, gliclazide, glimepiride, glipizide, gliquidone, glisoxepid, glyburide, glyhexamide, metformin, miglitol, nateglinide, orlistat, phenbutamide, pioglitazone, repaglinide, rosiglitazone, tolazamide, tolbutamide, tolcyclamide, tolrestat, troglitazone, voglibose and their salts.

Examples of antiemetics are alprazolam benzquinamide, benztropine, betahistine, chlorpromazine, dexamethasone, difenidol, dimenhydrinate, diphenhydramine, dolasetron, domperidone, dronabinol, droperidol, granisetron, haloperidol, lorazepam, meclizine, methylprednisolone, metoclopramide, ondansetron, perphenazine, prochlorperazine, promethazine, scopolamine, tributine, triethylperazine, triflupromazine, trimethobenzamide, tropisetron and their salts.

Examples of antiglaucoma agents are alprenoxime, dapiprazole, dipivefrin, latanoprost, naboctate, pirnabine and their salts.

Examples of antihistamines are acrivastine, activastine, albuterol, azelastine, bitolterol, alimemazine, amlexanox, azelastine, benzydamine, brompheniramine, cetirizine, chlorpheniramine, cimetidine, clemastine, cycloheptazine, cyproheptadine, diclofenac, diphenhydramine, dotarizine, ephedrine, epinastine, epinephrine, ethylnorepinephrine, fenpoterol, fexofenadine, flurbiprofen, hydroxyzine, ibuprofen, isoetharine, isoproterenol, ipratropium bromide, ketorolac, levocetirizine, loratidine, mequitazine, metaproterenol, phenylephrine, phenylpropanolamine, pirbuterol, promethazine, pseudoepedrine, pyrilamine, salmeterol, terbutaline, tranilast, xanthine derivatives, xylometazoline and their salts.

Examples of anti-infective agents are abacavir, albendazole, amantadine, amphotericin, amikacin, aminosalicylic acid, amoxycillin, ampicillin, amprenavir, atovaquin, azithromycin, aztreonam, carbenicillin, cefaclor, cefadroxil, cefamandole, cefazolin, cefdinir, cefepime, cefexime, cefoperazone, cefotaxime, cefotitam, cefoperazone, cefoxitin, cefpodoxine, cefprozil, ceftazidime, ceftibuten, ceftizoxime, ceftriaxone, cefuroxime, cephalexin, chloroquine, cidofovir, cilastatin, ciprofloxacin, clarithromycin, clavulinic acid, clindamycin, colistimethate, dalfopristine, dapsone, daunorubicin, delavirdin, demeclocycline, didanosine, doxycycline, doxorubicin, efavirenz, enoxacin, erythromycin, ethambutol, ethionamide, famsiflovir, fluconazole, flucytocin, foscarnet, fosfomycin, ganciclavir, gatifloxacin, griseofulvin, hydroxychloroquine, imipenem, indinavir, interferon, isoniazide, itraconazole, ivermectil, ketoconazole, lamivudine, levofloxacin, linizolid, lomefloxacin, lovacarbef, mebendazole, mefloquine, meropenem, methanamine, metronidazole, minocycline, moxefloxacin, naldixic acid, nelfinavir, neomycin, nevirapine, nitorfurantoin, norfloxacin, ofloxacin, oseltamivir, oxytetracycline, palivizumab, penicillins, perfloxacin, piperacillin, praziquantel, pyrazinamide, pyrimethamine, quinidine, quinupristine, retonavir, ribavirin, rifabutine, rifampicin, rimantadine, saquinavir, sparfloxacin, stavudine, streptomycin, sulfamethoxazole, teramycin, terbinafine, tetracycline, ticarcillin, thiabendazole, tobramycin, trimethoprim, trimetraxate, troleandomycin, trovafloxacin, valacyclovir, vancomycin, zalcitabine, zanamivir, zidovudine and their salts.

Examples of antiparkinsons are amantadine, adrogolide, altinicline, benztropine, biperiden, brasofensine, bromocriptine, budipine, cabergoline, CHF-1301, dihydrexidine, entacapone, etilevodopa, idazoxan, iometopane, lazabemide, melevodopa, carbidopa/levodopa, mofegiline, moxiraprine, pergolide, pramipexole, quinelorane, rasagiline, ropinirole, seligiline, talipexole, tolcapone, trihexyphenidyl and their salts.

Examples of antirheumatic agents are azathiprine, betamethasone, celecoxib, cyclosporin, diclofenac, hydroxychloroquine, indomethacin, infliximab, mercaptobutanedioic acid, methylprednisolone, naproxen, penicillamine, piroxicam, prednisolone, sulfasalazine and their salts.

Examples of platelet agents are abciximab, anagrelide, aspirin, cilostazol, clopidogrel, dipyridamole, epoprostenol, eptifibatide, ticlopidine, tinofiban and their salts.

Examples of antispasmodics and anticholinergic agents are aspirin, atropine, diclofenac, hyoscyamine, mesoprostol, methocarbamol, phenobarbital, scopolamine and their salts.

Examples of antitussives are acetaminophen, acrivastin, albuterol, benzonatate, beractant, brompheniramine, caffeine, calfactant, carbetapentane, chlorpheniramine, codeine, colfuscerin, dextromethorpham, dornase alpha, doxylamine, epinephrine, fexofenadine, guaphenesin, ipratropium, levalbuterol, metaproterenol, montelukast, pentoxyphyline, phenylephrine, phenylpropanolamine, pirbuterol, poractant alpha, pseudoephedrine, pyrilamine, salbuterol, salmeterol, terbutaline, theophylline, zafirlukast, zileuton and their salts.

Examples of carbonic anhydrase inhibitors are acetazolamide, dichlorphenamide, dorzolamide, methazolamide, sezolamide and their salts.

Examples of cardiovascular agents are abciximab, acebutolol, activase, adenosine, adrenaline, amidarone, amiloride, amlodipine, amyl nitrate, atenolol, atorvastatin, benzepril, bepiridil, betaxalol, bisoprolol, candesartan, captopril, cartenolol, carvedilol, cerivastatin, chlorthalidone, chlorthiazole, clofibrate, clonidine, colestipol, colosevelam, digoxinm, diltiazem, disopyramide, dobutamine, dofetilide, doxazosin, enalapril, epoprostenol, eprosartan, esmolol, ethacrynate, erythrityl, felodipine, fenoidapam, fosinopril, flecamide, fluorosemide, fluvastatin, gemfibrozil, hydrochlorthiazide, hydroflumethazine, ibutilide, indapamide, isosorbide, irbesartan, labetolol, lacidipine, lisinopril, losartan, lovastatin, mecamylamine, metaprolol, metaminol, metazolone, methylchlothaizide, methyldopa, metyrosine, mexiletine, midrodine, milrinonr, moexipril, nadolol, niacin, nicardipine, nicorandil, nifidepine, nimodipine, nisoldipine, nitroglycerin, phenoxybenzamine, perindopril, polythiazide, pravastatin, prazosin, procainamide, propafenone, propranolol, quanfacine, quinapril, quinidine, ranipril, reteplase, simvastatin, sotalol, spironolactone, streptokinase, telmisartan, terazosin, timolol, tocainamide, torsemide, trandolapril, triamterene, trapidil, valsartan and their salts.

Examples of cholinesterase inhibitors are donepezil, edrophonium, neostigmine, pyridostigmine, rivastigmine, tacrine and their salts.

Examples of CNS stimulants are caffeine, doxapram, dexoamphetamine, donepezil, edorphonium, methamphetamine, methylphenidate, modafinil, neostigmine, pemoline, phentermine, pyriodstigmine, rivastigmine, tacrin and their salts.

Examples of contraceptives are desogestral, ethinyl estradiol, ethynodiol, levonorgestrel, medroxyprogesterone, mestranol, norgestimate, norethindrone, norgestrel and their salts.

Examples of cystic fibrosis management are dornase alpha, pancrelipase, tobramycin and their salts.

Examples of dopamine receptor agonists are amantadine, cabergoline, fenoldopam, pergolide, pramipezal, ropinirole and their salts.

Examples of drugs used for endometriosis management are danazol, goserelin, leuprolide, nafarelin, norethindrone and their salts.

Examples of drugs used for erectile dysfunction therapy are alprostadil, sildenafil, yohimbine and their salts.

Examples of fertility agents are citrorelix, clomiphen, follitropin, ganirelix, gonadotropin, menotropin, progesterone, urofollitropin and their salts.

Examples of gastrointestinal agents are alosetron, bisacodyl, bismuth subsalicylate, celecoxib, difoxin, dipheoxylate, docusate, famotidine, glycopyrrolate, infliximab, lansoprazole, loperamide, metaclopramide, nizatidine, omeprazole, pantoprazole, rabeprazole, ranitidine, simethicone, sucralfate, and their salts.

Examples of immunomodulators and immunosupressives are azathioprin, ceftizoxine, cyclosporin, daclizumab, glatiramer, immunoglobulin, interferon, leflunomide, levamisol, mycophenolate, mausomanab, phthalidomide, ribavirine, sirolimus and their salts.

Examples of drugs used in alzheimer's disease are CP 118954, donepezil, galanthamine, metrifonate, revastigmine, tacrine, TAK-147 and their salts.

Examples of drugs used for migraine preparations are acetaminophen, dihyroergotamine, divalproex, ergotamine, propranolol, risatriptan, sumitriptan, trimetrexate and their salts. Examples of muscle relaxants are alcuronium-chloride, azapropazon, atracurium, baclofen, carisoprodol, quinine derivatives, chloromezanon, chlorophenesincarbamate, chlorozoxazon, cyclobenzaprine, dantrolen, decamethoniumbromide, dimethyltubocurariniumchloride, doxacurium, fenyramidol, gallamintriethiodide, guaiphensine, hexafluoreniumbromide, hexacarbacholinbromide, memantin, mephenesin, meprobamate, metamisol, metaxalon, methocarbamol, mivacurium, orphenadrin, pancuronium, phenazon, phenprobamate, pipecuronium, rapacuronium, rocuronium, succinylcholine, suxamethoniumchloride, tetrazepam, tizanidine, tubocurarine chloride, tybamate, vecuronium and their salts.

In preferred embodiments of the gastric retention controlled drug delivery system the muscle relaxant used is baclofen or its pharmaceutically acceptable salt. A baclofen gastric retention controlled drug delivery system is not known or disclosed or suggested prior to the present invention.

Baclofen may be used in the system in an amount ranging from about 15 mg to about 80 mg. In the gastric retention controlled drug delivery system of the present invention, baclofen is used in an amount of 30 mg. The system is designed such that a large part of the 30 mg dose of baclofen is present in the core, and is available as controlled release, while a small part of the drug is present in the coat, and is available as immediate release. Thus, a biphasic release of baclofen is provided by the delivery system of the present invention.

Examples of nucleoside analogues are abacavir, acyclovir, didanosine, gamciclovir, gemcitabine, lamivudine, ribavirin, stavudine, zalcitabine and their salts.

Examples of drugs used for osteoporosis management are alendronate, calcitonin, estradiol, estropipate, medroxyprogesterone, norethindrone, norgestimate, pamidronate, raloxifen, risdronate, zoledronate and their salts.

Examples of parasympathomimetics are bethanechol, piperidine, edrophonium, glycopyrolate, hyoscyamine, pilocarpine, tacrine, yohimbine and their salts.

Examples of prostaglandins are alprostadil, epoprostenol, misoprostol and their salts.

Examples of psychotherapeutic agents are acetophenazine, alentemol, alpertine, alprazolam, amitriptyline, apriprazole, azaperone, batelapine, befipiride, benperidol, benzindopyrine, bimithil, biriperone, brofoxine; bromperidol; bromperidol, bupropion, buspirone, butaclamol, butaperazine; butaperazin, carphenazine, carvotroline, cericlamine, chlorazepine, chlordiazepoxide, chlorpromazine; chlorprothixene, cinperene, cintriamide, citalopram, clomacran, clonazepam, clopenthixol, clopimozide, clopipazan, cloroperone, clothiapine, clothixamide, clozapine; cyclophenazine, dapiprazole, dapoxetine, desipramine, divalproex, dipyridamole, doxepin, droperidol, duloxetine, eltoprazine, eptipirone, etazolate, fenimide, flibanserin, flucindole, flumezapine, fluoxetine, fluphenazine, fluspiperone, fluspirilene, flutroline, fluvoxamine, gepirone, gevotroline, halopemide, haloperidol, hydroxyzine, hydroxynortriptyline, iloperidone, imidoline, lamotrigine, loxapine, enperone, mazapertine, mephobarbital, meprobamate, mesoridazine, mesoridazine, milnacipran, mirtazepine, metiapine, milenperone, milipertine, molindone, nafadotride, naranol, nefazodone, neflumozide, ocaperidone, odapipam, olanzapine, oxethiazine, oxiperomide, pagoclone, paliperidone, paroxitene, penfluridol, pentiapine perphenazine, phenelzine, pimozide, pinoxepin, pipamperone, piperacetazine, pipotiazine, piquindone, pirlindole, pivagabine, pramipexole, prochlorperazine, prochlorperazine, promazine, quetiapine, reboxetine, remoxipride, remoxipride, risperidone, rimcazole, robolzotan, selegiline, seperidol, sertraline, sertindole; seteptiline, setoperone, spiperone, sunipitron, tepirindole, thioridazine, thiothixene, tiapride, tioperidone, tiospirone, topiramate, tranylcypromine, trifluoperazine, trifluperidol, triflupromazine, triflupromazine, trimipramine, venlafaxine, ziprasidone and their salts.

Examples of sedatives, hypnotics and tranquilisers are bromazepam, buspirone, clazolam, clobazam, chlorazepate, diazepam, demoxepam, dexmedetomitine, diphenyhydramine, doxylamine, enciprazine, estrazolam, hydroxyzine, ketazolam, lorazatone, lorazepam, loxapine, medazepam, meperidine, methobarbital, midazolam, nabilone, nisobamate, oxazepam, pentobarbital, promethazine, propofol, triazolam, zaleplon, zolpidem and their salts.

Examples of drugs used for treatment of skin ailments are acitretin, alclometasone, allitretinoin, betamethasone, calciprotrine, chlorhexidine, clobetasol, clocortolone, clotriamozole, collagenase, cyclosporin, desonide, difluorosone, doxepine, eflornithine, finasteride, fluocinolone, flurandrenolide, fluticasone, halobetasol, hydrochloroquine, hydroquinone, hydroxyzine, ketoconazole, mafenide, malathion, menobenzone, neostigmine, nystatin, podofilox, povidone, tazorotene, tretinoin and their salts.

Examples of steroids and hormones are alclometasone, betamethasone, calcitonin, citrorelix, clobetasol, clocortolone, cortisones, danazol, desmopressin, desonide, desogestrel, desoximetasone, dexamethasone, diflorasone, estradiol, estrogens, estropipate, ethynlestradiol, fluocinolone, flurandrenolide, fluticasone, glucagon, gonadotropin, goserelin, halobetasol, hydrocortisone, leuprolide, levonorgestrel, levothyroxine, medroxyprogesterone, menotropins, methylprednisolone, methyltestosterone, mometasone, naferelin, norditropin, norethindrone, norgestrel, octreolide, oxandrolone, oxymetholone, polytropin, prednicarbate, prednisolone, progesterone, sermorelin, somatropin, stanozolol, testosterone, urofollitropin and their salts.

In accordance with this invention the core achieves a high degree of swelling in a short time. This high degree of swelling may be achieved by using highly and rapidly swellable polymers, or by avoiding a high pressure of compaction of the swellable polymers, or by use of highly swellable polymers that inherently compress to a low density. When the core that is compressed has a low density, the core has sufficient strength such that if it has to be further coated by compression then it can be transferred mechanically from the first compression station, where it is compressed, to the second compression station, where the compression coat is formed; or if it is to be further coated by spraying, then it can withstand the rigors of agitation in the coating equipment.

Examples of the highly swellable polymers that may be used in the present invention include:

highly swellable grades of cellulose ethers such as hydroxy $C_{1-4}$ alkyl $C_{1-4}$ alkyl celluloses, carboxyalkyl celluloses, hydroxy $C_{1-4}$ alkyl celluloses preferably hydroxyethylcellulose, hydroxypropylcellulose, hydroxypropyl methylcellulose, more preferably a high viscosity grade of hydroxyethylcellulose;

gums of plant, animal, mineral or synthetic origin such as (i) agar, alginates, carrageenan, furcellaran derived from marine plants, (ii) guar gum, gum arabic, gum tragacanth, karaya gum, locust bean gum, pectin derived from terrestrial plants, (iii) microbial polysaccharides such as dextran, gellan gum, rhamsan gum, welan gum, xanthan gum, and (iv) synthetic or semi-synthetic gums such as propylene glycol alginate, hydroxypropyl guar and modified starches like sodium starch glycolate;

a superdisintegrant polymer such as cross-linked polyvinylpyrrolidone, cross-linked sodium carboxymethylcellulose, carboxymethyl starch, sodium carboxymethyl starch, potassium methacrylate-divinylbenzene copolymer, polyvinyl alcohols, amylose, cross-linked amylose, starch derivatives, microcrystalline cellulose and cellulose derivatives, alpha-, beta- and gamma-cyclodextrin and dextrin derivatives;

an acrylic acid polymer such as cross-linked polymer available under the tradename Carbopol®;

a vinyl pyrrolidone polymer such as crosslinked polyvinylpyrrolidone or crospovidone; copolymers of vinyl pyrrolidone and vinyl acetate; or mixtures thereof.

In preferred embodiments the highly swellable polymer is a mixture of a superdisintegrant and one or more binding agents, the binding agent being selected from hydrophilic polymers, preferably highly swellable polymers. In preferred embodiments, the hydrophilic polymer used is a high viscosity cellulose derivative having aqueous solution viscosity ranging from about 500 mPas to about 1,20,000 mPas. A mixture of sodium starch glycolate and high viscosity grade hydroxyethyl cellulose is used as the preferred swellable polymer in one embodiment of the present invention. In yet another embodiment, the highly swellable polymer used is a mixture of sodium starch glycolate, high viscosity grade hydroxyethyl cellulose and hydroxypropyl methylcellulose.

Sodium starch glycolate is a sodium salt of carboxymethyl ether of starch having a molecular weight in the range of 500,000 to 1,000,000 Daltons, and is commercially available as Explotab® and Primojel®. Sodium starch glycolate causes disintegration by rapid uptake of water, followed by rapid and enormous swelling. The advantage of using sodium starch glycolate as the superdisintegrant is that its effectiveness is not affected by the presence of hydrophobic excipients, such as lubricants, or by increased compression pressure. It is capable of swelling to 300 times its volume in water. Sodium starch glycolate is used as the preferred superdisintegrant in the present invention in an amount ranging from about 5% to about 50% by weight of the core, preferably from about 10% to about 40% by weight of the core, more preferably from about 15% to about 30% by weight of the core.

Hydroxyethyl cellulose is a non-ionic, water soluble polymer, which is a partially substituted poly(hydroxyethyl)ether of cellulose, and is available in different grades that vary in viscosity and degree of substitution. It is commercially available as Cellosize from Amerchol Corp., and Natrosol® from Aqualon. Preferably, hydroxyethyl cellulose having aqueous solution viscosity ranging from 9000 mPas to 30,000 mPas for a 2% w/v aqueous solution is used as the hydrophilic polymer in the present invention. It is used in an amount ranging from about 5% to about 50% by weight of the core, preferably from about 10% to about 40% by weight of the core, more preferably from about 15% to about 30% by weight of the core.

Hydroxypropyl methylcellulose (HPMC) is a partly O-methylated and O-(2-hydroxypropylated) cellulose, available in different grades that vary in viscosity. The molecular weight of HPMC ranges between 10,000 and 1,500,000. It is commercially available as Benecel MHPC, Methocel and Metolose. In one embodiment of the present invention, HPMC K4M grade is used as the swelling polymer in an amount ranging from about 5% to about 25% by weight of the core, more preferably from about 10% to about 15% by weight of the core.

In preferred embodiments the mixture of high viscosity grade hydroxyethyl cellulose and sodium starch glycolate is used as the highly swellable polymer, preferably in a weight ratio lying in the range of 1:9 to 9:1, more preferably 3:7 to 7:3 and still more preferably 4:6 to 6:4, of hydroxyethyl cellulose:sodium starch glycolate. The cores formed with this mixture are capable of swelling rapidly and achieving floatation while maintaining their physical integrity over prolonged periods of time.

The gas generating agent used in the core of the gastric retention controlled drug delivery system of the present invention may include a single component that generates gas upon contact with the gastric fluid, or may include a gas generating couple. Gas generating components that may be used in the present invention include carbonates such as calcium carbonate, bicarbonates such as sodium or potassium bicarbonate, sulfites such as sodium sulfite, sodium bisulfite, or sodium metabisulfite, and the like. These salts may be used alone or in combination with an acid source as a gas generating couple. The acid source may be an edible organic acid, a salt of an edible organic acid, or mixtures thereof. Examples of organic acids that may be used include citric acid, malic acid, succinic acid, tartaric acid, fumaric acid, maleic acid, ascorbic acid, glutamic acid, and their salts, and mixtures thereof. The gas generating agent is used in an amount ranging from about 1% to about 50% by weight of the core, more preferably from about 1% to about 15% by weight of the core. Sodium bicarbonate is used as the preferred gas generating agent.

The highly swellable polymer may further comprise an excipient that increases the rate of swelling of the delivery system. This excipient may be a water-soluble compound that induces osmosis, or a wicking agent such as microcrystalline cellulose, that promotes the influx of water into the system. Water-soluble compounds suitable for inducing osmosis, i.e. osmotic agents or osmogents, include all pharmaceutically acceptable and pharmacologically inert water-soluble compounds referred to in the pharmacopoeias such as United States Pharmacopoeia, as well as in Remington: The Science and Practice of Pharmacy. Pharmaceutically acceptable water-soluble salts of inorganic or organic acids, or non-ionic organic compounds with high water solubility, e.g. carbohydrates such as sugar, or amino acids, are generally preferred. The examples of agents used for inducing osmosis include inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like, and mixtures thereof. In preferred embodiments, the core of the gastric retention controlled drug delivery system includes one or more osmotic agents that increase the rate of swelling of the system. Preferably, the osmotic agent is used in an amount ranging from about 0.5% to about 50% by weight of the core, more preferably from about 2% to about 40% by weight of the core.

The gastric retention controlled drug delivery system of the present invention may also include various pharmaceutically acceptable excipients, for example disintegrants such as starch, cellulose derivatives, gums, crosslinked polymers and the like; binders such as starch, gelatin, sugars, cellulose derivatives, polyvinyl pyrrolidone and the like; lubricants such as talc, magnesium stearate, colloidal silicon dioxide, polyethylene glycol, cellulose derivatives and the like; and mixtures thereof.

In preferred embodiments, hydroxypropyl methylcellulose (HPMC) is used as the binder. Preferably, HPMC K4M is used as the binder in an amount ranging from about 0.2% to about 5% by weight of the core, more preferably from about 0.2% to about 2% by weight of the core.

Examples of lubricants that may be used in the present invention include talc, magnesium stearate, calcium stearate, aluminum stearate, stearic acid, hydrogenated vegetable oils, colloidal silicon dioxide, polyethylene glycol, cellulose derivatives such as carboxyalkyl cellulose and its alkali salts, or mixtures thereof. In preferred embodiments, the lubricant used is a mixture of silicified microcrystalline cellulose, talc and polyethylene glycol. Silicified microcrystalline cellulose is a synergistic, intimate physical mixture of microcrystalline cellulose and colloidal silicon dioxide, having a particle size in the range of 20 to 200 μm, and generally contains 2% by weight of colloidal silicon dioxide. It is commercially available as Prosolv® SMCC, and has an improved compaction property as compared to microcrystalline cellulose. The polyethylene glycol (PEG) used is PEG 8000. The mixture is used as the lubricant in an amount ranging from about 0.5% to about 40% by weight of the core, preferably from about 5% to about 30% by weight of the core, more preferably from about 10% to about 25% by weight of the core.

The core of the gastric retention controlled drug delivery system is surrounded by a rapidly releasing coat composition comprising the same drug as in the core, and pharmaceutically acceptable excipients. In a preferred embodiment of the present invention, the coat composition comprises baclofen and pharmaceutically acceptable excipients, such as film forming agents, plasticisers and the like. The film forming agents are selected from a group comprising cellulose ethers and esters such as methyl cellulose, ethyl cellulose, hydroxypropyl cellulose, hydroxypropyl methylcellulose (HPMC); acrylic acid polymers such as methacrylate and methyl methacrylate copolymers, and the like, and mixtures thereof. In preferred embodiments hydroxypropyl methylcellulose is used as the film forming agent in an amount ranging from about 0.5% to about 5% by weight of the core, preferably from about 1% to about 3% by weight of the core. The rapidly releasing composition may further contain one or more plasticisers selected from a group comprising glycerin, propylene glycol, polyethylene glycols, acetylated monoglyceride, citrate esters such as triethyl citrate, and phthalate esters such as diethyl phthalate. In preferred embodiments propylene glycol is used as the plasticiser. Alternatively, hydroxypropyl methylcellulose coating solution, commercially available as Opadry® II from Colorcon, may be mixed with the drug and used to coat the controlled release cores.

The manufacture of coated tablets may be performed in two steps. In the first manufacturing step the core composition is added to the die cavity at a first compression station, compressed and ejected with the aid of a lower punch. The second step consists of applying a coat on the core by conventional methods such as spray coating or compression coating. Spray coating comprises exposing the surfaces of the core by rolling it in a suitable coating vessel or by fluidizing them in a fluidizing equipment; and applying coating compositions containing drug and coating polymers. The drug is incorporated either in the same composition containing the coating polymer in a liquid vehicle or is layered as a powder. Compression coating comprises filling the coating composition for the lower half of the tablet into the die at a second compression station, transfer of the core from the first compression station to the second compression station and its placement in the center of the coating composition already filled into the die, filling of the upper half of the coating composition into the die, a compression phase to form the coated tablet, and an ejection phase that serves to remove the compression coated tablet from the die with the aid of the lower punch.

The gastric retention controlled drug delivery system of the present invention rapidly swells while maintaining its physical integrity in gastrointestinal fluids for prolonged periods. A low density is achieved by entrapment of the gas generated by the gas generating agent such that the system floats in gastric fluids. The swelling and gas entrapment can occur rapidly such that the system is capable of achieving floatation in a dissolution bath containing 0.1N HCl in 15 minutes, preferably in less than 10 minutes.

The following examples do not limit the scope of the invention and are used as illustrations.

Example 1

The gastric retention controlled drug delivery system was obtained as per Table 1 below.

TABLE 1

| Ingredients | Quantity (mg/tablet) |
|---|---|
| Core | |
| Intragranular | |
| Baclofen | 20.0 |
| Lactose | 30.0 |
| Hydroxyethyl cellulose (HEC 250 H) | 400.0 |
| Sodium starch glycolate | 150.0 |
| Sodium bicarbonate | 40.0 |
| Hydroxypropyl methylcellulose (HPMC K4M) | 136.0 |
| Extragranular | |
| Silicified microcrystalline cellulose (Prosolv SMCC 90) | 90.0 |
| Talc | 24.0 |
| Polyethylene glycol (PEG 8000) | 10.0 |
| Hydroxypropyl methylcellulose (HPMC K4M) | 100.0 |
| Coat | |
| Baclofen | 10.0 |
| Hydroxypropyl methylcellulose (Opadry II) | 45.0 |

The core of the gastric retention controlled drug delivery system was obtained by passing baclofen, lactose, hydroxyethyl cellulose, sodium starch glycolate, sodium bicarbonate and a part of HPMC K4M through ASTM (American Society for Testing and Materials) sieve #40 and mixing the ingredients to obtain a dry powder blend. An aqueous solution of HPMC K4M was then used to granulate the dry powder blend. The granules thus obtained were passed through a suitable sieve and dried. The dry granules were lubricated with a mixture of Prosolv SMCC 90, talc, PEG 8000 and HPMC K4M, and compressed to obtain the cores. The cores were then coated with an aqueous solution containing baclofen and Opadry II to obtain the gastric retention controlled drug delivery system of the present invention.

The tablets thus obtained were subjected to dissolution testing at 37° C. using United States Pharmacopoeia Type II (paddle) dissolution apparatus at 50 rpm. The dissolution medium used was 1000 ml of 0.1N HCl. The tablets achieved floatation in about 10 minutes. The results of the dissolution test are recorded in Table 2 below.

TABLE 2

| Time | % drug released in 0.1N HCl |
|---|---|
| 0 | 0 |
| 1 | 39 |
| 2 | 44 |
| 4 | 53 |
| 6 | 60 |
| 8 | 66 |
| 12 | 77 |

Example 2

The gastric retention controlled drug delivery system was obtained as per Table 3 below—

TABLE 3

| Ingredients | Quantity (mg/tablet) |
|---|---|
| Core | |
| *Intragranular* | |
| Baclofen | 22.5 |
| Mannitol 60 | 260.0 |
| Hydroxyethyl cellulose (HEC 250 HX Pharma) | 200.0 |
| Sodium starch glycolate | 250.0 |
| Sodium bicarbonate | 80.0 |
| Hydroxypropyl methylcellulose (HPMC K4M) | 4.50 |
| *Extragranular* | |
| Silicified microcrystalline cellulose (Prosolv SMCC 90) | 90.0 |
| Talc | 24.0 |
| Polyethylene glycol (PEG 8000) | 10.0 |
| Coat | |
| Baclofen | 7.5 |
| Hydroxypropyl methylcellulose (HPMC E5) | 24.0 |
| Talc | 10.0 |
| Propylene glycol | 5.0 |
| Titanium dioxide | 11.0 |

The core of the gastric retention controlled drug delivery system was obtained by passing baclofen, mannitol, hydroxyethyl cellulose, sodium starch glycolate and sodium bicarbonate through ASTM (American Society for Testing and Materials) sieve #40 and mixing the ingredients to obtain a dry powder blend. An aqueous solution of HPMC K4M was then used to granulate the dry powder blend. The granules thus obtained were passed through a suitable sieve and dried. The dry granules were lubricated with a mixture of Prosolv SMCC 90, talc and PEG 8000, and compressed to obtain the cores. The cores were then coated with a hydroalcoholic solution of a mixture of baclofen, HPMC E5, talc, propylene glycol and titanium dioxide to obtain the gastric retention controlled drug delivery system of the present invention.

The tablets thus obtained were subjected to dissolution testing at 37° C. using United States Pharmacopoeia Type II (paddle) dissolution apparatus at 50 rpm. The dissolution medium used was 1000 ml of 0.1N HCl. The tablets achieved floatation in about 6 minutes. The results of the dissolution test are recorded in Table 4 below.

TABLE 4

| Time | % drug released in 0.1N HCl |
|---|---|
| 0 | 0 |
| 1 | 55 |
| 2 | 63 |
| 4 | 75 |
| 6 | 83 |
| 8 | 91 |
| 12 | 99 |

Example 3

The gastric retention controlled drug delivery system of the present invention was obtained as given in Table 5 below.

TABLE 5

| Ingredients | Quantity (mg/tab) |
|---|---|
| Baclofen | 30.0 |
| Hydroxy ethyl cellulose (Natrosol 250 H) | 197.5 |
| Sodium starch glycolate | 217.5 |
| Microcrystalline cellulose (Avicel PH 101) | 435.0 |
| Sodium bicarbonate | 10.0 |
| Polyvinylpyrrolidone (PVP K-30) | 22.0 |
| Talc | 9.0 |
| Magnesium stearate | 9.0 |

A part of baclofen, hydroxyethylcellulose, a part of sodium starch glycolate, a part of microcrystalline cellulose and a part of polyvinylpyrrolidone, were mixed together and granulated with isopropanol and lubricated with talc and magnesium stearate to form the core granulation. The remaining parts of baclofen, microcrystalline cellulose, polyvinylpyrrolidone and sodium starch glycolate were mixed together and granulated with water to form the coat granulation. The core granulations were compressed and the coat was applied on the core using compression coating. The gastric retention controlled drug delivery system thus obtained in the form of coated tablets shows a high degree of swellability in a short time, has sufficient strength for handling as well as remaining intact in aqueous fluids, and is capable of providing a biphasic controlled release profile.

Example 4

The pharmacokinetics of baclofen after administration of the gastric retention controlled drug delivery system comprising 30 mg baclofen (Example 2) was studied. A multiple-dose and single-dose, open label, randomized, comparative and two-way crossover study was undertaken for the same.

The pharmacokinetic assessment was based on the plasma levels of baclofen measured by blood sampling. Blood samples were obtained before dosing and at the following times after administration of the test medication—0.25, 0.5, 1, 1.5, 2, 2.5, 3, 4, 6, 8, 12, 12.5, 13, 13.5, 14, 15, 16, 20 and 24 hours.

Twelve healthy male volunteers were enrolled for the study and all of them completed the study. The subjects were fasted overnight and were given a high fat breakfast before dosing. Drinking water was prohibited 2 hours before dosing and 2 hours thereafter, but was allowed ad lib at all other times. Standard meals were provided at 4 hours and 8 hours after dosing and at appropriate times thereafter. Meal plans were identical for both the periods.

Subjects received a single gastric retention controlled release tablet of baclofen (30 mg) with 240 ml of water at ambient temperature after the fast, for five days.

The plasma concentration of baclofen was determined for samples collected at different time points and averaged over the twelve volunteers. The data is given in Table 6 below. The plasma concentration versus time profile is illustrated in FIG. 1.

TABLE 6

| Time (hours) | Mean Plasma concentration (ng/ml) of baclofen gastric retention controlled release tablet (30 mg) |
| --- | --- |
| 0 | 0 |
| 0.25 | 0.97 |
| 0.5 | 12.95 |
| 1.0 | 81.57 |
| 1.5 | 117.42 |
| 2.0 | 141.46 |
| 2.5 | 154.1 |
| 3.0 | 157.67 |
| 4.0 | 172.88 |
| 6.0 | 155.77 |
| 8.0 | 119.55 |
| 12.0 | 67.38 |
| 12.5 | 65.28 |
| 13.0 | 60.20 |
| 13.5 | 57.01 |
| 14.0 | 52.26 |
| 15.0 | 48.18 |
| 16.0 | 40.07 |
| 20.0 | 28.03 |
| 24.0 | 18.87 |

The gastric retention controlled drug delivery system was suitable for once daily administration.

The invention claimed is:

1. An oral controlled drug delivery system for once-a-day therapy comprising baclofen and release rate controlling excipients, wherein the said system is adapted to release baclofen in a controlled manner so as to provide control over the plasma levels, such that the plasma levels of baclofen are within a desirable range over a 24-hour period for said once-a-day therapy.

* * * * *